United States Patent
Foerster et al.

(10) Patent No.: US 10,576,306 B2
(45) Date of Patent: *Mar. 3, 2020

(54) COSMETIC PRODUCT INCLUDING A POLAR SOLVENT AND A THICKENER IN A FLASH EVAPORATION DEVICE

(71) Applicant: Henkel AG & Co. KGaA, Duesseldorf (DE)

(72) Inventors: Thomas Foerster, Duesseldorf (DE); Rolf Bayersdoerfer, Hamburg (DE); Thorsten Knappe, Schenefeld (DE)

(73) Assignee: Henkel AG & Co. KGaA (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/615,593

(22) Filed: Jun. 6, 2017

(65) Prior Publication Data

US 2017/0266467 A1    Sep. 21, 2017

Related U.S. Application Data

(63) Continuation of application No. PCT/EP2015/075373, filed on Nov. 2, 2015.

(30) Foreign Application Priority Data

Dec. 10, 2014   (DE) .......................... 10 2014 225 424

(51) Int. Cl.
| | | |
|---|---|---|
| *A61Q 5/06* | (2006.01) | |
| *A61K 8/02* | (2006.01) | |
| *A61K 8/30* | (2006.01) | |
| *A61K 8/81* | (2006.01) | |

(52) U.S. Cl.
CPC .............. *A61Q 5/06* (2013.01); *A61K 8/0204* (2013.01); *A61K 8/30* (2013.01); *A61K 8/8147* (2013.01); *A61K 2800/40* (2013.01); *A61K 2800/48* (2013.01)

(58) Field of Classification Search
CPC ........ A61K 8/34; A61K 8/8152; A61K 8/046; A61K 8/0204; A61K 8/30; A61K 8/8147; A61K 2800/48; A61K 2800/40; A61K 2800/87; A61Q 5/06
See application file for complete search history.

(56) References Cited

U.S. PATENT DOCUMENTS

| | | |
|---|---|---|
| 3,372,840 A | 3/1968 | Kelley |
| 5,030,443 A | 7/1991 | Varco et al. |
| 2002/0074349 A1 | 6/2002 | Michaels et al. |
| 2002/0079377 A1 | 6/2002 | Nichols |
| 2004/0065683 A1 | 4/2004 | Taylor et al. |
| 2007/0160552 A1 | 7/2007 | Sakakibara |
| 2012/0201774 A1* | 8/2012 | Schweinsberg ........ A61K 8/042 424/70.13 |
| 2013/0018333 A1* | 1/2013 | Thomason .......... A61M 35/003 604/290 |

FOREIGN PATENT DOCUMENTS

| | | |
|---|---|---|
| EP | 1634579 A1 | 3/2006 |
| JP | 2007319234 A | 12/2007 |
| WO | 200183071 A1 | 11/2001 |

OTHER PUBLICATIONS

PCT International Search Report (PCT/EP2015/075373) dated Feb. 1, 2016.
BASF: "Acrylic terpolymer products for hair-setting preparations with a strong, long-lasting effect (Luvimer)", Technical Information BASF, Sep. 1, 2000 (Sep. 1, 2000), pp. 1-21, XP007931915, p. 11; example 02/278.

* cited by examiner

*Primary Examiner* — Blessing M Fubara
(74) *Attorney, Agent, or Firm* — P. Scott Smith

(57) ABSTRACT

Disclosed is a cosmetic product comprising a) a cosmetic preparation that has a viscosity of 5,000 to 1,000,000 mPas and contains, in relation to the total weight of the preparation, a1) 60 to 98 wt % of at least one polar solvent; a2) 0.01 to 10 wt % of at least one thickener; b) a device for flash evaporating cosmetic preparation a). Also disclosed are a method using corresponding products and the use of cosmetic preparation a) as a process material in a flash evaporation device.

12 Claims, No Drawings

COSMETIC PRODUCT INCLUDING A POLAR SOLVENT AND A THICKENER IN A FLASH EVAPORATION DEVICE

FIELD OF THE INVENTION

The present invention generally relates to the technical field of the temporary reshaping of keratin-containing fibers, particularly human hairs. The object of the application are specific hair-cosmetic formulations that are suitable for application on keratin-containing fibers by means of a flash evaporation method. Furthermore, the use of these hair-cosmetic formulations in flash evaporation devices and methods for the temporary reshaping of keratin-containing fibers are also the object of the present invention.

BACKGROUND OF THE INVENTION

An attractive hairstyle is generally regarded today as an indispensable part of a groomed appearance. Based on current fashion trends, hairstyles are regarded time and time again as being chic which can be set up and/or maintained for an extended period up to several days using only setting agents. Hair treatment products that serve to permanently or temporarily shape the hair therefore play an important role. While the chemical structure of the keratin-containing fibers is modified through reduction and oxidation during permanent reshaping, such modifications of the chemical structure do not take place during temporary reshaping. Such products for temporary shaping usually include synthetic polymers and/or waxes as the setting agent.

The most important characteristic of a product for temporarily shaping keratin-containing fibers, hereinafter also called styling product, is that the greatest possible hold is given to the treated fibers in their newly modeled shape—i.e., a shape that is impressed upon the fibers. If the keratin-containing fibers are human hairs, this is also referred to as a strong hairstyle hold or high holding strength of the styling product. The hairstyle hold is determined substantially by the type and quantity of the setting agents used, although the other components of the styling product and the form of application can also have an impact.

The spray application of appropriate cosmetic preparations has great significance in the region of the temporary deformation of keratin-containing fibers, with the preparations generally being applied as pump sprays or aerosol sprays. For this purpose, the cosmetic preparations are packaged in a dispensing device from which they are sprayed through a valve either by means of mechanical force effect or with the aid of a propellant. Both methods have obvious drawbacks. While pump sprays are generally not suitable for the long-lasting uniform spay application of hair-cosmetic preparations, aerosol sprays are based on the use of propellants or propellant gases, which, on the one hand, do not have any cosmetic effect and, on the other hand, pose a danger if handled improperly.

Against this background, a need exists for alternative ways to atomize hair-cosmetic preparations. Flash evaporation has proven its worth as such an alternative spraying method. In this method, which is described in international patent application WO 200183071 A1 (Henkel), for example, a liquid or pasty solvent-containing composition is heated in an enclosed space to a temperature above the boiling point of the solvent, thus producing overpressure in the composition. Upon relaxation (throttling) of the pressure, the liquid vaporizes the liquid and can then be atomized by means of a suitable nozzle, for example.

Therefore, even if flash evaporation is suitable in principle for the spray application of hair-cosmetic preparations, but not every hair-cosmetic preparation can be simultaneously atomized by means of a flash evaporation method. On the one hand, this is due to the heating of the cosmetic preparation required for flash evaporation; on the other hand, it is due to the specifics of the atomized spray produced as a result of flash evaporation, such as the size of the droplets produced and droplet density in the atomized spray.

BRIEF SUMMARY OF THE INVENTION

It was therefore the object of the present invention to make available specific hair-cosmetic preparations for temporarily deformation of keratin-containing fibers that are suitable for targeted spray application by means of a flash evaporation device by virtue of their chemical and physical characteristics. Moreover, the preparations should be suitable for achieving a high level of holding strength, particularly long-lasting holding strength, and a high-volume effect after application using a flash evaporation method. It was found that, from among the multitude of effective hair-cosmetic polymer preparations, solvent-containing preparations with a specific viscosity are particularly suitable for achieving this object.

A first object of the present invention is therefore a cosmetic product comprising
a) a cosmetic preparation with a viscosity from 5,000 to 1,000,000 mPas which includes, with respect to its total weight,
  a1) 60 to 98 wt % of at least one polar solvent;
  a2) 0.01 to 10 wt % of at least one thickener;
b) a device for flash-evaporating the cosmetic preparation a).

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The viscosity is determined using a Brookfield model D220 viscometer (20° C., spindle 6, 5 rpm).

The cosmetic preparation a) is a liquid. It can also be present as a solution or dispersion, for example as an emulsion or suspension. Preferred cosmetic preparations a) are present in the form of a solution or suspension. Specific viscosity values have proven to be especially advantageous for the application characteristics of cosmetic preparations. Preferred cosmetic preparations a) are therefore characterized in that their viscosity is 10,000 to 50,000 mPas, preferably 20,000 to 250,000 mPas.

As a first essential component, the cosmetic preparation according to the invention includes 60 to 98 wt % of at least one polar solvent a1). Preferred cosmetic products are characterized in that the proportion by weight of the polar solvent a1) to the total weight of the cosmetic preparation a) is 70 to 98 wt %, preferably 80 to 95 wt %. Such agents are characterized by a good cosmetic effect with simultaneously good applicability.

To improve the application characteristics of cosmetic preparations according to the invention while simultaneously minimizing the thermal loading of any active ingredients and adjuvants during the flash evaporation method, it has proven advantageous to use solvents a1) having a boiling temperature (20° C., 1013 mbar) between 50 and 110° C., preferably between 70 and 105° C. Ethanol, isopropanol, and water have proven to be especially suitable, for which reason they are preferred as polar solvents a1).

Especially preferred polar solvents a1) or solvent systems are characterized in that
the proportion by weight of water and ethanol to the total weight of the polar solvent a1) is preferably at least 60 wt %, more preferably at least 80 wt %, especially preferably at least 90 wt %, and particularly at least 95 wt %;
the polar solvent a1), with respect to its total weight, comprises greater than 80 wt %, preferably greater than 88 wt %, and particularly greater than 92 wt % water.

One specific embodiment is characterized in that the polar solvent a1) comprises water and ethanol and the weight ratio of water to ethanol is 5:1 to 1:5, preferably 2:1 to 1:2, and particularly 5:4 to 4:5.

A second essential component of cosmetic compositions according to the invention is the thickener a2). With regard to the manufacturability, applicability and cosmetic effect of cosmetic compositions according to the invention, it has proven advantageous if the proportion by weight of the thickener a2) with respect to the total weight of the cosmetic preparation a) is 0.05 to 8.0 wt %, preferably 0.1 to 5.0 wt %.

Preferred thickeners are selected from the group of the polymeric organic thickeners. The polymeric organic thickeners can be crosslinked or non-crosslinked.

A first group of especially preferred thickeners a2) include at least one structural unit selected from at least one structural unit of formula (I) or salt forms thereof or at least one structural unit (II) or salt forms thereof,

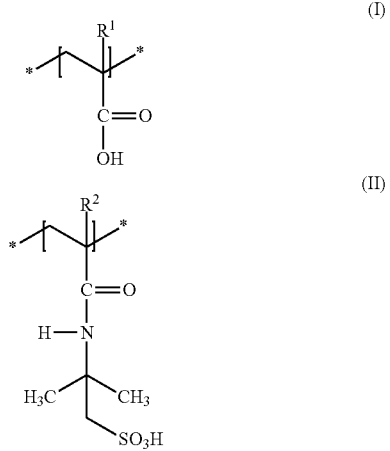

where $R^1$ and $R^2$, independently of one another, stand for a hydrogen atom or a methyl group.

According to the above formulas and all of the formulas that follow, a chemical bond that is designated by the symbol * stands for a free valence of the corresponding structural fragment.

Especially preferred anionic, thickening polymers include at least one structural unit of formula (I). Acrylic acid homopolymers constitute a first group of especially preferred thickeners a2).

Especially preferred thickeners are polyacrylic acids with the INCI designation carbomer, such as those sold by 3V Sigma under the trade name Synthalen® K or by Lubrizol under the trade name Carbopol, for example.

A second especially preferred group of thickeners a2) is formed by the polymeric, anionic, amphiphilic thickeners. Corresponding thickeners preferably comprise at least one structural unit of formula (III) and at least one structural unit of formula (IV).

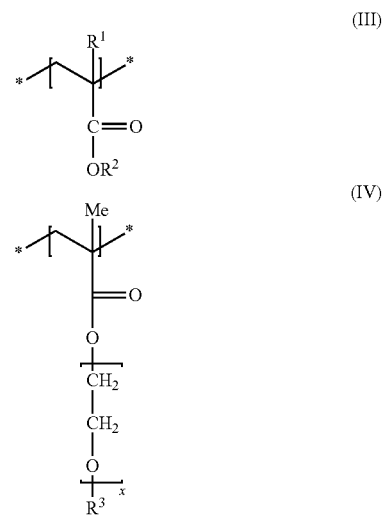

where
$R^1$ stands for a hydrogen atom or a methyl group,
$R^2$ stands for a hydrogen atom or a ($C_1$ bis $C_6$) alkyl group,
$R^3$ stands for a ($C_8$ bis $C_{30}$) alkyl group,
$M^+$ stands for a physiologically acceptable cation, and
x stands for an integer from 0 to 35.

Especially preferred thickeners are particularly those with the INCI designations acrylates/beheneth-25 methacrylate copolymer, acrylates/ceteth-20 itaconate copolymer, acrylates/ceteth-20 methacrylate copolymer, acrylates/laureth-25 methacrylate copolymer, acrylates/palmeth-20 acrylate copolymer, acrylates/palmeth-25 acrylate copolymer, acrylates/palmeth-25 itaconate copolymer and acrylates/steareth-50 acrylate copolymer.

Especially preferred thickeners are
thickeners with the INCI designation acrylates/steareth-20 methacrylate copolymer, such as those sold under the trade name Aculyn® 22 by Rohm & Haas, for example;
thickeners with the INCI designation acrylates/steareth-20 methacrylate crosspolymer such as those sold under the trade name Aculyn® 88 by Rohm & Haas, for example;
thickeners with the INCI designation acrylates/steareth-20 itaconate copolymer, such as those sold under the trade name Structure 2001 by National Starch, for example.

Other polymeric, amphiphilic thickeners are characterized by long-chain alkyl substituents. This group includes the compounds with the INCI designations acrylates/stearyl methacrylate copolymer, acrylates/vinyl isodecanoate crosspolymer.

Especially preferred thickeners are
thickeners with the INCI designation acrylates/$C_{10-30}$ alkyl acrylate crosspolymer, such as those sold under the trade name Carbopol Ultrez 21 by Lubrizol, for example.

Other thickeners a2) can be selected, for example, from among the polymeric thickening agents known under the following INCI designations: acrylamides copolymer, acrylamide/sodium acrylate copolymer, acrylamide/sodium acryloyldimethyltaurate copolymer, acrylates/acetoacetoxyethyl methacrylate copolymer, acrylic acid/acrylonitrogens copolymer, agar, agarose, alcaligenes polysaccharides, algin, alginic acid, ammonium acrylates/acrylonitrogens copolymer, ammonium acrylates copolymer, ammonium acryloyldimethyltaurate/vinyl formamide copolymer, ammonium acryloyldimethyltaurate/VP copolymer, ammonium alginate, ammonium polyacryloyldimethyl taurate, amylopectin, ascorbyl methylsilanol pectinate, astragalus gummifer gum, attapulgite, *Avena sativa* (oat) kernel flour, bentonite, butoxy chitosan, caesalpinia spinosa gum, calcium alginate, calcium carboxymethyl cellulose, calcium carrageenan, calcium potassium carbomer, calcium starch octenylsuccinate, C20-40 alkyl stearate, carboxybutyl chitosan, carboxymethyl chitin, carboxymethyl chitosan, carboxymethyl dextran, carboxymethyl hydroxyethylcellulose, carboxymethyl hydroxypropyl guar, cellulose acetate propionate carboxylate, cellulose gum, ceratonia siliqua gum, cetyl hydroxyethylcellulose, cholesterol/HDI/pullulan copolymer, cholesteryl hexyl dicarbamate pullulan, cyamopsis tetragonoloba (guar) gum, diglycol/CHDM/isophthalates/SIP copolymer, dihydrogenated tallow benzylmonium hectorite, dimethicone crosspolymer-2, dimethicone propyl PG-betaine, DMAPA acrylates/acrylic acid/acrylonitrogens copolymer, ethylene/sodium acrylate copolymer, gelatin, gellan gum, glyceryl alginate, glycine soja (soybean) flour, guar hydroxypropyltrimonium chloride, hectorite, hydrated silica, hydrogenated potato starch, hydroxybutyl methylcellulose, hydroxyethyl acrylate/sodium acryloyldimethyl taurate copolymer, hydroxyethylcellulose, hydroxyethyl chitosan, hydroxyethyl ethylcellulose, hydroxypropylcellulose, hydroxypropyl chitosan, hydroxypropyl ethylenediamine carbomer, hydroxypropyl guar, hydroxypropyl methylcellulose, hydroxypropyl methylcellulose stearoxy ether, hydroxystearamide MEA, isobutylene/sodium maleate copolymer, lithium magnesium silicate, lithium magnesium sodium silicate, macrocystis pyrifera (kelp), magnesium alginate, magnesium aluminum silicate, magnesium silicate, magnesium trisilicate, methoxy PEG-22/dodecyl glycol copolymer, methylcellulose, methyl ethylcellulose, methyl hydroxyethylcellulose, microcrystalline cellulose, montmorillonite, moroccan lava clay, natto gum, nonoxynyl hydroxyethylcellulose, octadecene/MA copolymer, pectin, PEG-800, PEG-crosspolymer, PEG-150/decyl alcohol/SMDI copolymer, PEG-175 diisostearate, PEG-190 distearate, PEG-15 glyceryl tristearate, PEG-140 glyceryl tristearate, PEG-240/HDI copolymer bis-decyltetradeceth-20 ether, PEG-100/IPDI copolymer, PEG-180/laureth-50/tmmg copolymer, PEG-10/lauryl dimethicone crosspolymer, PEG-15/lauryl dimethicone crosspolymer, PEG-2M, PEG-5M, PEG-7M, PEG-9M, PEG-14M, PEG20M, PEG-23M, PEG-25M, PEG-45M, PEG-65M, PEG-90M, PEG-115M, PEG-160M, PEG-120 methyl glucose trioleate, PEG-180/octoxynol-40/TMMG copolymer, PEG-150 pentaerythrityl tetrastearate, PEG-4 rapeseedamide, PEG-150/stearyl alcohol/SMDI copolymer, polyacrylate-3, polyacrylic acid, polycyclopentadiene, polyether-1, polyethylene/isopropyl maleate/MA copolyol, polymethacrylic acid, polyquaternium-52, polyvinyl alcohol, potassium alginate, potassium aluminum polyacrylate, potassium carbomer, potassium carrageenan, potassium polyacrylate, potato starch modified, PPG-14 laureth-60 hexyl dicarbamate, PPG-14 laureth-60 isophoryl dicarbamate, PPG-14 palmeth-60 hexyl dicarbamate, propylene glycol alginate, PVP/decene copolymer, PVP montmorillonite, rhizobian gum, ricinoleic acid/adipic acid/AEEA copolymer, sclerotium gum, sodium acrylate/acryloyldimethyl taurate copolymer, sodium acrylates/acrolein copolymer, sodium acrylates/acrylonitrogens copolymer, sodium acrylates copolymer, sodium acrylates/vinyl isodecanoate crosspolymer, sodium acrylate/vinyl alcohol copolymer, sodium carbomer, sodium carboxymethyl chitin, sodium carboxymethyl dextran, sodium carboxymethyl beta-glucan, sodium carboxymethyl starch, sodium carrageenan, sodium cellulose sulfate, sodium cyclodextrin sulfate, sodium hydroxypropyl starch phosphate, sodium isooctylene/MA copolymer, sodium magnesium fluorosilicate, sodium polyacrylate, sodium polyacrylate starch, sodium polyacryloyldimethyl taurate, sodium polymethacrylate, sodium polystyrene sulfonate, sodium silicoaluminate, sodium starch octenylsuccinate, sodium stearoxy PG-hydroxyethylcellulose sulfonate, sodium styrene/acrylates copolymer, sodium tauride acrylates/acrylic acid/acrylonitrogens copolymer, *Solanum tuberosum* (potato) starch, starch/acrylates/acrylamide copolymer, starch hydroxypropyltrimonium chloride, steareth-60 cetyl ether, steareth-100/PEG-136/HDI copolymer, sterculia urens gum, synthetic fluorphlogopite, tamarindus indica seed gum, tapioca starch, TEA-alginate, TEA-carbomer, *Triticum vulgare* (wheat) starch, tromethamine acrylates/acrylonitrogens copolymer, tromethamine magnesium aluminum silicate, welan gum, yeast beta-glucan, yeast polysaccharides, *Zea mays* (corn) starch.

Besides the cosmetic preparation a), the cosmetic products according to the invention further comprise a flash evaporation device. In the framework of the present invention, the term "flash evaporation" refers to the occurrence of vapor upon reduction of the pressure in a closed space that is filled with liquid and is under overpressure (with respect to the environment). Such overpressure can be produced, for example, by heating a quantity of the cosmetic preparation a) in an enclosed space to a temperature T1. In the closed space, the liquid has a pressure saturated vapor pressure p1 at a given temperature T1. For example, if the closed space is opened by means of a valve, for example, to a relaxation space that is not at overpressure (pressure $p_0$<p1), then the pressure in the previously closed space drops and the cosmetic preparation a), or the solvent included in the cosmetic preparation or parts of this solvent, vaporizes during the propagation of the new pressure level. The resulting vapor or atomized spray can be utilized for the application of specific cosmetic preparations.

Therefore, if the cosmetic preparation a) is heated starting from standard conditions ($T_0$=25° C., $p_0$=1,000 bar) in a closed space, this results in both increased temperature and increased pressure of the cosmetic preparation a). This increased pressure can be relieved in a relaxation space to a pressure $p_0$, for example to the ambient air pressure ($p_0$=1,000 bar), whereby an at least partial evaporation of the cosmetic preparation a) is achieved.

The cosmetic preparation a) can be decompressed directly in the space in which it was previously heated. Alternatively, however, the heated cosmetic preparation a), which is under overpressure, can also transported after heating to a second space in which decompression then occurs.

In other words, flash evaporation is a process in which the cosmetic preparation a) is heated in a closed container by means of a heating device to temperatures above the ambient temperature, with pressure occurring in the container that is above the ambient pressure, and the heated cosmetic preparation a), now under increased pressure, is then released from the container into the environment.

Accordingly, a flash evaporation device is a device which comprises a container and a heating device and is embodied such that a cosmetic preparation a) in the closed container can be heated by means of the heating device to temperatures above the ambient temperature in such a way that a pressure above the ambient pressure occurs in the container and the heated cosmetic preparation a), now under increased pressure, can be released from the container into the environment.

At the same time as or after the pressure release, the cosmetic preparation a) can be fed to a nozzle by means of which characteristics of the vapor or atomized spray produced by the flash evaporation, particularly the droplet size or the droplet density, or even the spray distance and the shape of the spray cone can be influenced. The use of nozzles, preferably atomizer nozzles, is therefore preferred. The specific type of nozzle or the specific nozzle structure is adopted in a targeted manner based on the respective atomized spray characteristics.

In summary, a preferred flash evaporation device comprises
b1) a container b1) to be closed and opened by means of a valve that defines the closed interior space in which the cosmetic preparation can be held,
b2) a heating device b2) that enables heating of a cosmetic preparation located in the container b1).

Especially preferably, an additional nozzle b3) is used which enables the atomization of the cosmetic preparation a) escaping from the container. As an alternative to a valve, a closing element that acts in a comparable manner and is capable of locking or releasing an associated opening in the container through an appropriate change in position can also be used.

A preferred object of the object of the present invention is a cosmetic product comprising
a) a cosmetic preparation including, with respect to its total weight,
　a1) 60 to 98 wt % of at least one polar solvent;
　a2) 0.01 to 10 wt % of at least one thickener;
b) a device for flash-evaporating the cosmetic preparation a), with the flash-evaporating device comprising a container b1) and a heating device b2) and being embodied such that
　the cosmetic preparation can be received in the interior space of the container b1),
　the interior of the container b1) filled at least in part with the cosmetic preparation a) can be sealed,
　the cosmetic preparation a) in the closed interior of the container b1) can be heated by means of the heating device b2), thereby increasing the pressure.

An especially preferred object of the object of the present invention is therefore a cosmetic product comprising
a) a cosmetic preparation with a viscosity from 5,000 to 1,000,000 mPas which includes, with respect to its total weight,
　a1) 60 to 98 wt % of at least one polar solvent;
　a2) 0.01 to 10 wt % of at least one thickener;
b) a device for flash-evaporating the cosmetic preparation a), comprising
　b1) a container b1) to be sealed and opened by means of a valve
　b2) a heating device that enables heating of a cosmetic preparation located in the container b1)
　b3) a nozzle b3) that enables atomization of the cosmetic preparation a).

In other words, an especially preferred object of the present invention is a cosmetic product, comprising
a) a cosmetic preparation including, with respect to its total weight,
　a1) 60 to 98 wt % of at least one polar solvent;
　a2) 0.01 to 10 wt % of at least one thickener;
b) a device for flash-evaporating the cosmetic preparation a), with the flash-evaporating device comprising a container b1) and a heating device b2) and being embodied such that
　the cosmetic preparation can be received in the interior space of the container b1),
　the interior of the container b1) filled at least in part with the cosmetic preparation a) can be sealed,
　the cosmetic preparation a) in the closed interior of the container b1) can be heated by means of the heating device b2), thereby increasing the pressure,
　the heated cosmetic preparation a) can be released from the interior of the container b1) under pressure reduction into the environment.

The container b1) in which the cosmetic preparation is heated is embodied in such a way that enables this container to be sealed off against the environment during the heating of the cosmetic preparation a) and to be opened after heating in order to enable flash evaporation of the cosmetic preparation a). This can be ensured by a component for flow regulation, for example, particularly a valve.

The container b1) in which the cosmetic preparation is heated is preferably in contact with another container, from which the quantity of the cosmetic preparation provided for flash evaporation is transferred into the container b1) before heating. The access between this reservoir and container b1) is opened and closed by means of a suitable device, such as a valve. This other container is preferably embodied in the form of a reservoir, that is, it holds several times, for example more than ten times, preferably more than fifty times the quantity of the cosmetic preparation required for the evaporation process. In other words, the other container/reservoir preferably holds several times, for example more than ten times the volume, preferably more than twenty times, and particularly more than fifty times the volume of the container b1).

Another especially preferred object of the present invention is therefore a cosmetic product, comprising
a) a cosmetic preparation including, with respect to its total weight,
　a1) 60 to 98 wt % of at least one polar solvent;
　a2) 0.01 to 10 wt % of at least one thickener;
b) a device for flash-evaporating the cosmetic preparation a), comprising
　b1) a container b1) to be sealed and opened by means of a valve
　b2) a heating device that enables heating of a cosmetic preparation located in the closed container b1)
　b3) a nozzle b3) that enables atomization of the cosmetic preparation a),
c) a reservoir for the cosmetic preparation a) from which the cosmetic preparation a) can reach the container b1), wherein
　the access between reservoir and container b1) has a component for flow regulation by means of which the flow of the cosmetic preparation a) from the reservoir into the container b1) can be interrupted;
　the reservoir has at least ten times the volume, preferably at least twenty times, and particularly fifty times the volume of the container b1).

The reservoir is not a pressurized container, and the cosmetic composition located in the reservoir is not under pressure; in other words, the pressure inside the reservoir corresponds to the ambient pressure (also called air pressure or atmospheric pressure). Therefore, corresponding cosmetic products do not include any propellant, for example. Nor does the cosmetic product have any pump device that is suitable for releasing or spraying the cosmetic preparation into the environment without the action of the flash evaporation device.

An especially preferred object of the present invention is therefore a cosmetic product, comprising
a) a cosmetic preparation including, with respect to its total weight,
  a1) 60 to 98 wt % polar solvent;
  a2) 0.01 to 10 wt % of at least one thickener;
b) a device for flash-evaporating the cosmetic preparation a), comprising
  b1) a container b1) to be sealed and opened by means of a valve
  b2) a heating device that enables heating of a cosmetic preparation located in the closed container b1)
  b3) a nozzle b3) that enables the atomization of the cosmetic preparation a);
c) a reservoir for the cosmetic preparation a) from which the cosmetic preparation a) can reach the container b1), wherein
  the access between reservoir and container b1) has a component for flow regulation by means of which the flow of the cosmetic preparation a) from the reservoir into the container b1) can be interrupted;
  the reservoir holds at least ten times the volume, preferably at least fifty times the volume of the container b1);
  the pressure on the interior of the reservoir corresponds to the ambient pressure.

An especially preferred object of the present invention is therefore a cosmetic product, comprising
a) a cosmetic preparation including, with respect to its total weight,
  a1) 60 to 98 wt % polar solvent;
  a2) 0.01 to 10 wt % of at least one thickener;
b) a device for flash-evaporating the cosmetic preparation a), comprising
  b1) a container b1) to be sealed and opened by means of a valve
  b2) a heating device that enables heating of a cosmetic preparation located in the closed container b1)
  b3) a nozzle b3) that enables atomization of the cosmetic preparation a).
c) a reservoir for the cosmetic preparation a) from which the cosmetic preparation a) can reach the container b1), wherein
  the access between reservoir and container b1) has a component for flow regulation by means of which the flow of the cosmetic preparation a) from the reservoir into the container b1) can be interrupted;
  the reservoir holds at least ten times the volume, preferably at least fifty times the volume of the container b1);
  the pressure on the interior of the reservoir corresponds to the ambient pressure, and the cosmetic product does not comprise any propellant.

Furthermore, cosmetic products are preferred which comprise
a) a cosmetic preparation including, with respect to its total weight,
  a1) 60 to 98 wt % polar solvent;
  a2) 0.01 to 10 wt % of at least one thickener;
b) a device for flash-evaporating the cosmetic preparation a), comprising
  b1) a container b1) to be sealed and opened by means of a valve
  b2) a heating device that enables heating of a cosmetic preparation located in the closed container b1)
  b3) a nozzle b3) that enables atomization of the cosmetic preparation a).
c) a reservoir for the cosmetic preparation a) from which the cosmetic preparation a) can reach the container b1), wherein
  the access between reservoir and container b1) has a component for flow regulation by means of which the flow of the cosmetic preparation a) from the reservoir into the container b1) can be interrupted;
  the reservoir holds at least ten times the volume, preferably at least fifty times the volume of the container b1);
  the pressure on the interior of the reservoir corresponds to the ambient pressure,
  and the cosmetic product does not have any pump device that is suitable for releasing or spraying the cosmetic preparation a) without the action of the flash evaporation device.

In summary, an especially preferred object of the present invention is therefore a cosmetic product, comprising
a) a cosmetic preparation including, with respect to its total weight,
  a1) 60 to 98 wt % polar solvent;
  a2) 0.01 to 10 wt % of at least one thickener;
b) a device for flash-evaporating the cosmetic preparation a), comprising
  b1) a container b1) to be sealed and opened by means of a valve
  b2) a heating device that enables heating of a cosmetic preparation located in the closed container b1)
  b3) a nozzle b3) that enables atomization of the cosmetic preparation a).
c) a reservoir for the cosmetic preparation a) from which the cosmetic preparation a) can reach the container b1), wherein
  the access between reservoir and container b1) has a component for flow regulation by means of which the flow of the cosmetic preparation a) from the reservoir into the container b1) can be interrupted;
  the reservoir holds at least ten times the volume, preferably at least fifty times the volume of the container b1);
  the pressure on the interior of the reservoir corresponds to the ambient pressure, and the cosmetic product does not comprise any propellant,
and the cosmetic product does not have any pump device that is suitable for releasing or spraying the cosmetic preparation a) without the action of the flash evaporation device.

Besides the two aforedescribed components a1) and a2), the cosmetic preparations a) according to the invention can include other active ingredients or adjuvants, with such active ingredients or adjuvants being preferred in particular which improve the manufacturability, applicability, and/or cosmetic effect of cosmetic preparations according to the invention.

One example of preferred additional active ingredient and adjuvant are the film-forming polymers a3), the use of which in the cosmetic agents according to the invention is especially preferred. Permanently and temporarily cationic, anionic, nonionic, or amphoteric polymers are suitable as film-forming polymers a3). These film-forming polymers can be of synthetic or natural origin. Preferred cosmetic preparations a) include, with respect to their total weight, 0, 1 to 20 wt %, preferably 0.5 to 15 wt %, and particularly 1.0 to 10%, of a film-forming polymer a3). This polymer a3) is different from the polymer a2).

Examples of common film-forming polymers a3) are acrylamides/ammonium acrylate copolymer, acrylamides/DMAPA acrylates/methoxy PEG methacrylate copolymer, acrylamidopropyltrimonium chloride/acrylamide copolymer, acrylamidopropyltrimonium chloride/acrylates copolymer, acrylates/acetoacetoxyethyl methacrylate copolymer, acrylates/acrylamide copolymer, acrylates/ammonium methacrylate copolymer, acrylates/t-butylacrylamide copolymer, acrylates copolymer, acrylates/$C_{1-2}$ succinates/hydroxyacrylates copolymer, acrylates/lauryl acrylate/stearyl acrylate/ethylamine oxide methacrylate copolymer, acrylates/octylacrylamide copolymer, acrylates/octylacrylamide/diphenyl amodimethicone copolymer, acrylates/stearyl acrylate/ethylamine oxide methacrylate copolymer, acrylates/VA copolymer, acrylates/VP copolymer, adipic acid/diethylenetriamine copolymer, adipic acid/dimethylaminohydroxypropyl diethylenetriamine copolymer, adipic acid/epoxypropyl diethylenetriamine copolymer, adipic acid/isophthalic acid/neopentyl glycol/trimethylolpropane copolymer, allyl stearate/VA copolymer, aminoethylacrylate phosphate/acrylates copolymer, aminoethylpropanediol-acrylates/acrylamide copolymer, aminoethylpropanediol-AMPD-acrylates/diacetoneacrylamide copolymer, ammonium VA/acrylates copolymer, AMPD-acrylates/diacetoneacrylamide copolymer, AMP-acrylates/allyl methacrylate copolymer, AMP-acrylates/$C_{1-18}$ alkyl acrylates/$C_{1-8}$ alkyl acrylamide copolymer, AMP-Acrylates/Diacetoneacrylamide Copolymer, AMP-acrylates/dimethylaminoethylmethacrylate copolymer, Bacillus/rice bran extract/soybean extract ferment filtrate, bis-butyloxyamodimethicone/PEG-60 copolymer, butyl acrylate/ethylhexyl methacrylate copolymer, butyl acrylate/hydroxypropyl dimethicone acrylate copolymer, butylated PVP, butyl ester of ethylene/MA copolymer, butyl ester of PVM/MA copolymer, calcium/sodium PVM/MA copolymer, corn starch/acrylamide/sodium acrylate copolymer, diethylene glycolamine/epichlorohydrin/piperazine copolymer, dimethicone crosspolymer, diphenyl amodimethicone, ethyl ester of PVM/MA copolymer, hydrolyzed wheat protein/PVP crosspolymer, isobutylene/ethylmaleimide/hydroxyethylmaleimide copolymer, isobutylene/MA copolymer, isobutylmethacrylate/bis-hydroxypropyl dimethicone acrylate copolymer, isopropyl ester of PVM/MA copolymer, lauryl acrylate crosspolymer, lauryl methacrylate/glycol dimethacrylate crosspolymer, MEA sulfite, methacrylic acid/sodium acrylamidomethyl propane sulfonate copolymer, methacryloyl ethyl betaine/acrylates copolymer, octylacrylamide/acrylates/butylaminoethyl methacrylate copolymer, PEG/PPG-25/25 dimethicone/acrylates copolymer, PEG-8/SMDI copolymer, polyacrylamide, polyacrylate-6, polybeta-alanine/glutaric acid crosspolymer, polybutylene terephthalate, polyester-1, polyethylacrylate, polyethylene terephthalate, polymethacryloyl ethyl betaine, polypentaerythrityl terephthalate, polyperfluoroperhydrophenanthrene, Polyquaternium-1, Polyquaternium-2, Polyquaternium-4, Polyquaternium-5, Polyquaternium-6, Polyquaternium-7, Polyquaternium-8, Polyquaternium-9, Polyquaternium-10, Polyquaternium-11, Polyquaternium-12, Polyquaternium-13, Polyquaternium-14, Polyquaternium-15, Polyquaternium-16, Polyquaternium-17, Polyquaternium-18, Polyquaternium-19, Polyquaternium-20, Polyquaternium-22, Polyquaternium-24, Polyquaternium-27, Polyquaternium-28, Polyquaternium-29, Polyquaternium-30, Polyquaternium-31, Polyquaternium-32, Polyquaternium-33, Polyquaternium-34, Polyquaternium-35, Polyquaternium-36, Polyquaternium-39, Polyquaternium-45, Polyquaternium-46, Polyquaternium-47, Polyquaternium-48, Polyquaternium-49, Polyquaternium-50, Polyquaternium-55, Polyquaternium-56, Polysilicone-9, Polyurethane-1, Polyurethane-6, Polyurethane-10, polyvinyl acetate, polyvinyl butyral, polyvinylcaprolactam, polyvinylformamide, polyvinyl imidazolinium acetate, polyvinyl methyl ether, potassium butyl ester of PVM/MA copolymer, potassium ethyl ester of PVM/MA copolymer, PPG-70 polyglyceryl-10 ether, PPG-12/SMDI copolymer, PPG-51/SMDI copolymer, PPG-10 sorbitol, PVM/MA copolymer, PVP, PVP/VA/itaconic Acid copolymer, PVP/VA/vinyl propionate copolymer, rhizobian gum, rosin acrylate, shellac, sodium butyl ester of PVM/MA copolymer, sodium ethyl ester of PVM/MA copolymer, sodium polyacrylate, sterculia urens gum, terephthalic acid/isophthalic acid/sodium isophthalic acid sulfonate/glycol copolymer, trimethylolpropane triacrylate, trimethylsiloxysilylcarbamoyl pullulan, VA/crotonates copolymer, VA/crotonates/methacryloxybenzophenone-1 copolymer, VA/crotonates/vinyl neodecanoate copolymer, VA/crotonates/vinyl propionate copolymer, VA/DBM copolymer, VA/vinyl butyl benzoate/crotonates copolymer, vinylamine/vinyl alcohol copolymer, vinyl caprolactam/VP/dimethylaminoethyl methacrylate copolymer, VP/acrylates/lauryl methacrylate copolymer, VP/dimethylaminoethylmethacrylate copolymer, VP/DMAPA acrylates copolymer, VP/hexadecene copolymer, VP/VA copolymer, VP/Vinyl caprolactam/DMAPA acrylates copolymer, yeast palmitate, and styrene/VP copolymer.

Especially preferably, cosmetic products are characterized in that the film-forming polymer a3) is selected from the group of the anionic polymers, preferably from the group of the copolymers of acrylic acid and methacrylic acid.

An especially preferred anionic acrylate copolymer a3) is constructed at least from the following monomer units: at least one (meth)acrylic acid unit (V), at least one (meth)acrylic acid alkyl ester unit (VI), and at least one (meth)acrylic acid hydroxyalkyl ester unit (VII). This preferred copolymer a3) can be constructed according to the invention from other monomer units. According to embodiments of the invention, however, the copolymer a3) is constructed only from the units (V), (VI), and (VII), that is, it consists of units derived from these monomer units.

The at least one methacrylic acid unit (V) can be a methacrylic acid or acrylic acid unit.

The alkyl group of the (meth)acrylic acid alkyl ester unit (VI) is preferably a $C_1$-$C_8$ alkyl residue that can be linear or branched. Examples of alkyl residues are methyl, ethyl, propyl, isopropyl, 1-butyl, 2-butyl, iso-butyl, tert-butyl, linear or branched pentyl, linear or branched hexyl, linear or branched heptyl and linear or branched octyl. More preferably, the alkyl group is a $C_1$ to $C_5$ alkyl group. According to one embodiment of the invention, two or more (meth)acrylic acid alkyl ester units (VI) are included which differ from one another with respect to the carbon number of the alkyl group. For example, a $C_1$-$C_3$ alkyl methacrylate unit and a $C_2$-$C_5$ alkyl acrylate unit are included.

The hydroxy alkyl residue of the (meth)acrylic acid hydroxy alkyl ester unit (VII) can be a hydroxy $C_1$-$C_{10}$ alkyl group, preferably a hydroxy $C_2$-$C_5$ alkyl residue. In a preferred embodiment, the (meth)acrylic acid hydroxy alkyl ester unit (VII) is a (meth)acrylic acid hydroxy ethyl ester.

The proportion of the units (V), (VI), and (VII) in the acrylate resin a3) can vary within wide limits. The proportion of unit (1) in the acrylate copolymer is preferably 2 to 50 wt %, more preferably 5 to 30 wt %. The proportion of unit (2) in the acrylate copolymer is preferably 5 to 95 wt %, more preferably 45 to 90 wt %. The proportion of unit (3) in the acrylate copolymer is preferably 2 to 70 wt %, more preferably 5 to 30 wt %.

Suitable anionic acrylate copolymers a3) are commercially available under the INCI designation acrylates/hydroxyesters acrylates copolymer. The most preferred is the anionic acrylate copolymer (a) Acudyne® 1000 from The Dow Chemical Company.

Another preferred anionic acrylate copolymer a3) comprises structural units of the formula (VIII), in which $R^1$ stands for a methyl group and $R^2$ stands for a methyl group, and structural units of the formula (VIII), in which $R^1$ stands for a hydrogen atom and $R^2$ stands for a butyl group (particularly for an n-butyl group), and structural units of the formula (IX), in which $R^3$ stands for a methyl group and $R^4$ stands for a 2-hydroxyethyl group, and structural units of the formula (X), in which $R^7$ stands for a methyl group at least one structural unit of the formula (XI), in which $R^5$ and $R^6$, independently of one another, stand for a hydrogen atom or a ($C_1$ to $C_6$) alkyl group, preferably for hydrogen

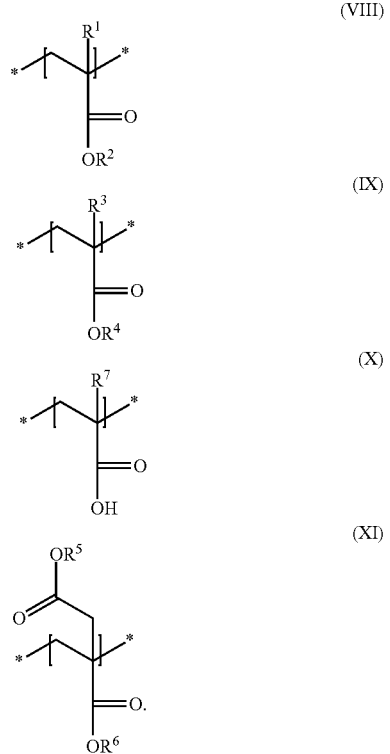

An especially preferred polymer bears the INCI nomenclature acrylates/$C_{1-2}$ succinates/hydroxyacrylates copolymer. It can be obtained from the Dow Company, for example, under the trade name Acudyne LT-120 (INCI nomenclature: acrylates/$C_{1-2}$ succinates/hydroxyacrylates copolymer).

A second group of polymers a3) that are preferably used in the cosmetic preparation are the vinyl pyrrolidone homo- or copolymers B. Some examples of polymers B that are especially preferably used are:

Polyvinyl pyrrolidones, such as those which are sold under the name Luviskol® (BASF), for example.

Vinyl pyrrolidone/vinyl ester copolymers, such as those which are sold under the trade name Luviskol® (BASF), for example. Luviskol® VA 64 and Luviskol® VA 73, each vinyl pyrrolidone/vinyl acetate copolymers, are preferred nonionic polymers.

Due to their cosmetic effect in combination with the copolymers a2), film-forming polymers that are preferably used according to the invention are particularly the polyvinyl pyrrolidones (INCI designation: PVP) as well as the vinyl pyrrolidone/vinyl acetate copolymers (INCI designation VP/VA copolymer). Preferred cosmetic products are characterized in that the film-forming polymer a3) is selected from the group of the nonionic polymers, preferably from the group of the polyvinyl pyrrolidone and vinyl pyrrolidone/vinyl acetate copolymers, preferably polyvinyl pyrrolidone.

A third group of especially preferred film-forming polymers a3) constitutes the group of the copolymers of methacryloylethyl-N,N-dimethylamine oxide.

In an especially suitable embodiment, the cosmetic preparation according to the invention includes at least one amphoteric setting polymer that is formed from at least one monomer selected from among acrylic acid, methacrylic acid, acrylic acid ethyl ester, methacrylic acid methyl ester, acrylic acid ethyl ester, methacrylic acid ethyl ester, acrylic acid propyl ester, methacrylic acid propyl ester, acrylic acid isopropyl ester, and methacrylic acid isopropyl ester, at least one second monomer different from the first, selected from among acrylic acid stearyl ester and methacrylic acid stearyl ester, and methacryloyl ethylamine oxide, particularly methacryloyl ethyl-N, N-dimethylamine oxide.

For example, these copolymers bear the INCI designation acrylates/stearyl acrylate/ethylamine oxide methacrylate copolymer and are available under the trade name Diaformer Z-632 from Clariant.

In one suitable embodiment, the cosmetic preparation according to the invention includes at least one amphoteric setting polymer that is formed from at least one monomer selected from among acrylic acid, methacrylic acid, acrylic acid methyl ester, methacrylic acid methyl ester, acrylic acid ethyl ester, methacrylic acid ethyl ester, acrylic acid propyl ester, methacrylic acid propyl ester, acrylic acid isopropyl ester, and methacrylic acid isopropyl ester, at least one second monomer different from the first, selected from among acrylic acid lauryl ester and methacrylic acid lauryl ester, at least one third monomer different from the first and second monomers, selected from among acrylic acid stearyl ester and methacrylic acid stearyl ester, and methacryloyl ethylamine oxide, particularly methacryloyl ethyl-N, N-dimethylamine oxide.

Corresponding copolymers with the INCI designation acrylates/lauryl acrylates/stearyl acrylate/ethylamine oxide methacrylate copolymer are available, for example, under the trade names Diaformer Z-712N and Diaformer Z-731N from Clariant.

A fourth group of especially preferred film-forming polymers a3) comprises copolymers a3) that can be attributed to the monomers i) N-tert-octylacrylamide, ii) acrylic acid, iii) tert.-butylaminoethyl methacrylate, as well as, optionally, other monomers.

Preferred copolymers a3) preferably consist of at least 90 wt %, preferably at least 95 wt % and particularly at least 97 wt % of the monomers N-tert-octylacrylamide, acrylic acid, and tert.-butylaminoethyl methacrylate. Especially preferred copolymers a3) have been obtained exclusively from the monomers N-tert-octylacrylamide, acrylic acid, and tert.-butyl amino ethyl methacrylate.

Copolymers a3) from the monomers i) N-tert-octylacrylamide, ii) acrylic acid, iii) tert.-butylaminoethyl methacrylate, iv) methyl methacrylate, and v) hydroxypropyl methacrylate are especially preferred.

The previously described copolymers a3) are sold by National Starch, for example, under the name Amphomer® (INCI designation: octylacrylamide/acrylates/butylaminoethyl methacrylate copolymer; CAS number 70801-07-9) from National Starch.

In order to improve its manufacturability, applicability, and cosmetic effect, the cosmetic preparation a) preferably includes nonionic surfactant a4), with especially preferred cosmetic preparations a) being characterized in that they include, with respect to their total weight, 0.02 to 4.0 wt %, preferably 0.05 to 2.0 wt %, and particularly 0.1 to 1.0 wt % nonionic surfactant a4).

Preferred nonionic surfactants are PEG derivatives of hydrated castor oil, which are available, for example, under the name PEG hydrogenated castor oil, e.g., PEG-30 hydrogenated castor oil, PEG-33 hydrogenated castor oil, PEG-35 hydrogenated castor oil, PEG-36 hydrogenated castor oil, PEG-40 hydrogenated castor oil, or PEG-60 hydrogenated castor oil. Nonionic surfactants selected from the group of the PEG derivatives of hydrated castor oil, especially preferably from the group PEG-40 hydrogenated castor oil and PEG-60 hydrogenated castor oil, particularly PEG-40 hydrogenated castor oil, are especially preferred according to the invention.

Another preferred component of cosmetic preparations a) according to the invention are the cationic surfactants a5). Preferred cationic surfactants a5) are selected from among quaternary ammonium compounds, esterquats, and amidoamines. The cationic surfactants are included in the cosmetic preparation a), with respect to the total weight thereof, in quantities from 0.05 to 3.0 wt %, preferably 0.1 to 2.0 wt %, and particularly 0.2 to 1.0 wt %. Cationic surfactants a5) from the group of the quaternary ammonium compounds are especially preferred.

Preferred quaternary ammonium compounds are ammonium halogenides, particularly chlorides and bromides, such as alkyltrimethylammonium chlorides, dialkyldimethylammonium chlorides and trialkylmethylammonium chlorides, e.g., cetyltrimethylammonium chloride, stearyltrimethylammonium chloride, distearyldimethylammonium chloride, lauryldimethylammonium chloride, lauryldimethylbenzylammonium chloride and tricetylmethylammonium chloride, as well as the imidazolium compounds known by the INCI designations quaternium-27 and quaternium-83. The long alkyl chains of the abovementioned surfactants preferably have 10 to 18 carbon atoms. Very especially preferred cosmetic preparations a) according to the invention are characterized in that they include, with respect to the total weight thereof, 0.05 to 3.0 wt %, preferably 0.1 to 2.0 wt %, and particularly 0.2 to 1.0 wt % ($C_{12}$ to $C_{18}$) alkyltrimethylammonium salt(s).

Other noteworthy active ingredients or adjuvants that are suitable are, in particular, additional nourishing ingredients.

For example, the agent can include at least one protein hydrolysate and/or a derivative thereof as a nourishing ingredient. Protein hydrolysates are product mixtures that are obtained through the acid-, alkali-, or enzyme-catalyzed decomposition of proteins. According to the invention, the term "protein hydrolysates" is understood as also referring to total hydrolysates and to individual amino acids and derivatives thereof, as well as to mixtures of different amino acids. The molecular weight of the protein hydrolysates that can be used according to the invention lies between 75, the molecular weight of glycine, and 200,000; preferably, the molecular weight is 75 to 50,000, and very especially preferably 75 to 20,000 Dalton.

The agent according to the invention can also include at least one vitamin, provitamin, vitamin precursor, and/or derivative thereof as a nourishing ingredient. Those vitamins, provitamins and vitamin precursors are preferred according to the invention which are usually associated with groups A, B, C, E, F and H.

Other nourishing ingredients are panthenol, caffeine, nicotinamide, and sorbitol.

Moreover, the agents according to the invention can also include at least one plant extract, or also mono- or oligosaccharides and/or lipids as nourishing ingredients.

The composition of several especially preferred cosmetic preparations according to the invention can be seen from the following tables (indicated in wt % with respect to the total weight of the cosmetic agent, unless indicated otherwise). As regards other preferred embodiments of these especially preferred compositions, the remarks concerning the preparations a) according to the invention apply mutatis mutandis.

|  | Formula 1 | Formula 2 | Formula 3 | Formula 4 | Formula 5 |
| --- | --- | --- | --- | --- | --- |
| Polar solvent a1) | 45 to 99 | 70 to 98 | 80 to 95 | 90 | 90 |
| Thickener a2) | 0.01 to 10 | 0.05 to 8.0 | 0.1 to 5.0 | 0.3 | 1.5 |
| Optional additives | Up to 100 | Up to 100 | Up to 100 | Up to 100 | Up to 100 |

|  | Formula 6 | Formula 7 | Formula 8 | Formula 9 | Formula 10 |
| --- | --- | --- | --- | --- | --- |
| Polar solvent a1) | 45 to 99 | 70 to 98 | 80 to 95 | 90 | 90 |
| Thickener a2) | 0.01 to 10 | 0.05 to 8.0 | 0.1 to 5.0 | 0.3 | 1.5 |
| Film-forming polymer a3) | 0.1 to 20 | 0.5 to 15 | 1.0 to 10 | 2.5 | 1.6 |
| Optional additives | Up to 100 | Up to 100 | Up to 100 | Up to 100 | Up to 100 |

|  | Formula 11 | Formula 12 | Formula 13 | Formula 14 | Formula 15 |
| --- | --- | --- | --- | --- | --- |
| Polar solvent a1) | 45 to 99 | 70 to 98 | 80 to 95 | 90 | 90 |
| Thickener a2) | 0.01 to 10 | 0.05 to 8.0 | 0.1 to 5.0 | 0.3 | 1.5 |
| Nonanionic surfactant a4) | 0.02 to 4.0 | 0.05 to 2.0 | 0.1 to 1.0 | 0.6 | 0.5 |
| Optional additives | Up to 100 | Up to 100 | Up to 100 | Up to 100 | Up to 100 |

-continued

|  | Formula 16 | Formula 17 | Formula 18 | Formula 19 | Formula 20 |
|---|---|---|---|---|---|
| Polar solvent a1) | 45 to 99 | 70 to 98 | 80 to 95 | 90 | 90 |
| Thickener a2) | 0.01 to 10 | 0.05 to 8.0 | 0.1 to 5.0 | 0.3 | 1.5 |
| Film-forming polymer a3) | 0.1 to 20 | 0.5 to 15 | 1.0 to 10 | 2.5 | 1.6 |
| Nonanionic surfactant a4) | 0.02 to 4.0 | 0.05 to 2.0 | 0.1 to 1.0 | 0.6 | 0.5 |
| Optional additives | Up to 100 | Up to 100 | Up to 100 | Up to 100 | Up to 100 |

|  | Formula 21 | Formula 22 | Formula 23 | Formula 24 | Formula 25 |
|---|---|---|---|---|---|
| Polar solvent a1) | 45 to 99 | 70 to 98 | 80 to 95 | 90 | 90 |
| Polyacrylic acid a2) | 0.01 to 10 | 0.05 to 8.0 | 0.1 to 5.0 | 0.3 | 1.5 |
| Optional additives | Up to 100 | Up to 100 | Up to 100 | Up to 100 | Up to 100 |

|  | Formula 26 | Formula 27 | Formula 28 | Formula 29 | Formula 30 |
|---|---|---|---|---|---|
| Polar solvent a1) | 45 to 99 | 70 to 98 | 80 to 95 | 90 | 90 |
| Polyacrylic acid a2) | 0.01 to 10 | 0.05 to 8.0 | 0.1 to 5.0 | 0.3 | 1.5 |
| Film-forming polymer a3) | 0.1 to 20 | 0.5 to 15 | 1.0 to 10 | 2.5 | 1.6 |
| Optional additives | Up to 100 | Up to 100 | Up to 100 | Up to 100 | Up to 100 |

|  | Formula 31 | Formula 32 | Formula 33 | Formula 34 | Formula 35 |
|---|---|---|---|---|---|
| Polar solvent a1) | 45 to 99 | 70 to 98 | 80 to 95 | 90 | 90 |
| Polyacrylic acid a2) | 0.01 to 10 | 0.05 to 8.0 | 0.1 to 5.0 | 0.3 | 1.5 |
| Nonanionic surfactant a4) | 0.02 to 4.0 | 0.05 to 2.0 | 0.1 to 1.0 | 0.6 | 0.5 |
| Optional additives | Up to 100 | Up to 100 | Up to 100 | Up to 100 | Up to 100 |

|  | Formula 36 | Formula 37 | Formula 38 | Formula 39 | Formula 40 |
|---|---|---|---|---|---|
| Polar solvent a1) | 45 to 99 | 70 to 98 | 80 to 95 | 90 | 90 |
| Polyacrylic acid a2) | 0.01 to 10 | 0.05 to 8.0 | 0.1 to 5.0 | 0.3 | 1.5 |
| Film-forming polymer a3) | 0.1 to 20 | 0.5 to 15 | 1.0 to 10 | 2.5 | 1.6 |
| Nonanionic surfactant a4) | 0.02 to 4.0 | 0.05 to 2.0 | 0.1 to 1.0 | 0.6 | 0.5 |
| Optional additives | Up to 100 | Up to 100 | Up to 100 | Up to 100 | Up to 100 |

|  | Formula 41 | Formula 42 | Formula 43 | Formula 44 | Formula 45 |
|---|---|---|---|---|---|
| Polar solvent a1) | 45 to 99 | 70 to 98 | 80 to 95 | 90 | 90 |
| Polymeric, anionic, amphiphilic thickener a2) | 0.01 to 10 | 0.05 to 8.0 | 0.1 to 5.0 | 0.3 | 1.5 |
| Optional additives | Up to 100 | Up to 100 | Up to 100 | Up to 100 | Up to 100 |

|  | Formula 46 | Formula 47 | Formula 48 | Formula 49 | Formula 50 |
|---|---|---|---|---|---|
| Polar solvent a1) | 45 to 99 | 70 to 98 | 80 to 95 | 90 | 90 |
| Polymeric, anionic, amphiphilic thickener a2) | 0.01 to 10 | 0.05 to 8.0 | 0.1 to 5.0 | 0.3 | 1.5 |
| Film-forming polymer a3) | 0.1 to 20 | 0.5 to 15 | 1.0 to 10 | 2.5 | 1.6 |
| Optional additives | Up to 100 | Up to 100 | Up to 100 | Up to 100 | Up to 100 |

|  | Formula 51 | Formula 52 | Formula 53 | Formula 54 | Formula 55 |
|---|---|---|---|---|---|
| Polar solvent a1) | 45 to 99 | 70 to 98 | 80 to 95 | 90 | 90 |
| Polymeric, anionic, amphiphilic thickener a2) | 0.01 to 10 | 0.05 to 8.0 | 0.1 to 5.0 | 0.3 | 1.5 |
| Nonanionic surfactant a4) | 0.02 to 4.0 | 0.05 to 2.0 | 0.1 to 1.0 | 0.6 | 0.5 |
| Optional additives | Up to 100 | Up to 100 | Up to 100 | Up to 100 | Up to 100 |

|  | Formula 56 | Formula 57 | Formula 58 | Formula 59 | Formula 60 |
|---|---|---|---|---|---|
| Polar solvent a1) | 45 to 99 | 70 to 98 | 80 to 95 | 90 | 90 |
| Polymeric, anionic, amphiphilic thickener a2) | 0.01 to 10 | 0.05 to 8.0 | 0.1 to 5.0 | 0.3 | 1.5 |
| Film-forming polymer a3) | 0.1 to 20 | 0.5 to 15 | 1.0 to 10 | 2.5 | 1.6 |
| Nonanionic surfactant a4) | 0.02 to 4.0 | 0.05 to 2.0 | 0.1 to 1.0 | 0.6 | 0.5 |
| Optional additives | Up to 100 | Up to 100 | Up to 100 | Up to 100 | Up to 100 |

-continued

|  | Formula 61 | Formula 62 | Formula 63 | Formula 64 | Formula 65 |
|---|---|---|---|---|---|
| Polar solvent a1) | 45 to 99 | 70 to 98 | 80 to 95 | 90 | 90 |
| Thickener a2) | 0.01 to 10 | 0.05 to 8.0 | 0.1 to 5.0 | 0.3 | 1.5 |
| Polyvinyl pyrrolidone a3) | 0.1 to 20 | 0.5 to 15 | 1.0 to 10 | 2.5 | 1.6 |
| Optional additives | Up to 100 | Up to 100 | Up to 100 | Up to 100 | Up to 100 |

|  | Formula 66 | Formula 67 | Formula 68 | Formula 69 | Formula 70 |
|---|---|---|---|---|---|
| Polar solvent a1) | 45 to 99 | 70 to 98 | 80 to 95 | 90 | 90 |
| Thickener a2) | 0.01 to 10 | 0.05 to 8.0 | 0.1 to 5.0 | 0.3 | 1.5 |
| Polyvinyl pyrrolidone a3) | 0.1 to 20 | 0.5 to 15 | 1.0 to 10 | 2.5 | 1.6 |
| Nonanionic surfactant a4) | 0.02 to 4.0 | 0.05 to 2.0 | 0.1 to 1.0 | 0.6 | 0.5 |
| Optional additives | Up to 100 | Up to 100 | Up to 100 | Up to 100 | Up to 100 |

|  | Formula 71 | Formula 72 | Formula 73 | Formula 74 | Formula 75 |
|---|---|---|---|---|---|
| Polar solvent a1) | 45 to 99 | 70 to 98 | 80 to 95 | 90 | 90 |
| Thickener a2) | 0.01 to 10 | 0.05 to 8.0 | 0.1 to 5.0 | 0.3 | 1.5 |
| Vinyl pyrrolidone/vinyl acetate copolymer a3) | 0.1 to 20 | 0.5 to 15 | 1.0 to 10 | 2.5 | 1.6 |
| Optional additives | Up to 100 | Up to 100 | Up to 100 | Up to 100 | Up to 100 |

|  | Formula 76 | Formula 77 | Formula 78 | Formula 79 | Formula 80 |
|---|---|---|---|---|---|
| Polar solvent a1) | 45 to 99 | 70 to 98 | 80 to 95 | 90 | 90 |
| Thickener a2) | 0.01 to 10 | 0.05 to 8.0 | 0.1 to 5.0 | 0.3 | 1.5 |
| Vinyl pyrrolidone/vinyl acetate copolymer a3) | 0.1 to 20 | 0.5 to 15 | 1.0 to 10 | 2.5 | 1.6 |
| Nonanionic surfactant a4) | 0.02 to 4.0 | 0.05 to 2.0 | 0.1 to 1.0 | 0.6 | 0.5 |
| Optional additives | Up to 100 | Up to 100 | Up to 100 | Up to 100 | Up to 100 |

|  | Formula 81 | Formula 82 | Formula 83 | Formula 84 | Formula 85 |
|---|---|---|---|---|---|
| Polar solvent a1) | 45 to 99 | 70 to 98 | 80 to 95 | 90 | 90 |
| Polyacrylic acid a2) | 0.01 to 10 | 0.05 to 8.0 | 0.1 to 5.0 | 0.3 | 1.5 |
| Polyvinyl pyrrolidone a3) | 0.1 to 20 | 0.5 to 15 | 1.0 to 10 | 2.5 | 1.6 |
| Optional additives | Up to 100 | Up to 100 | Up to 100 | Up to 100 | Up to 100 |

|  | Formula 86 | Formula 87 | Formula 88 | Formula 89 | Formula 90 |
|---|---|---|---|---|---|
| Polar solvent a1) | 45 to 99 | 70 to 98 | 80 to 95 | 90 | 90 |
| Polyacrylic acid a2) | 0.01 to 10 | 0.05 to 8.0 | 0.1 to 5.0 | 0.3 | 1.5 |
| Polyvinyl pyrrolidone a3) | 0.1 to 20 | 0.5 to 15 | 1.0 to 10 | 2.5 | 1.6 |
| Nonanionic surfactant a4) | 0.02 to 4.0 | 0.05 to 2.0 | 0.1 to 1.0 | 0.6 | 0.5 |
| Optional additives | Up to 100 | Up to 100 | Up to 100 | Up to 100 | Up to 100 |

|  | Formula 91 | Formula 91 | Formula 93 | Formula 94 | Formula 95 |
|---|---|---|---|---|---|
| Polar solvent a1) | 45 to 99 | 70 to 98 | 80 to 95 | 90 | 90 |
| Polyacrylic acid a2) | 0.01 to 10 | 0.05 to 8.0 | 0.1 to 5.0 | 0.3 | 1.5 |
| Vinyl pyrrolidone/vinyl acetate copolymer a3) | 0.1 to 20 | 0.5 to 15 | 1.0 to 10 | 2.5 | 1.6 |
| Optional additives | Up to 100 | Up to 100 | Up to 100 | Up to 100 | Up to 100 |

|  | Formula 96 | Formula 97 | Formula 98 | Formula 99 | Formula 100 |
|---|---|---|---|---|---|
| Polar solvent a1) | 45 to 99 | 70 to 98 | 80 to 95 | 90 | 90 |
| Polyacrylic acid a2) | 0.01 to 10 | 0.05 to 8.0 | 0.1 to 5.0 | 0.3 | 1.5 |
| Vinyl pyrrolidone/vinyl acetate copolymer a3) | 0.1 to 20 | 0.5 to 15 | 1.0 to 10 | 2.5 | 1.6 |
| Nonanionic surfactant a4) | 0.02 to 4.0 | 0.05 to 2.0 | 0.1 to 1.0 | 0.6 | 0.5 |
| Optional additives | Up to 100 | Up to 100 | Up to 100 | Up to 100 | Up to 100 |

|  | Formula 101 | Formula 102 | Formula 103 | Formula 104 | Formula 105 |
|---|---|---|---|---|---|
| Polar solvent a1) | 45 to 99 | 70 to 98 | 80 to 95 | 90 | 90 |
| Polymeric, anionic, amphiphilic thickener | 0.01 to 10 | 0.05 to 8.0 | 0.1 to 5.0 | 0.3 | 1.5 |

-continued

| | | | | | |
|---|---|---|---|---|---|
| Polyvinyl pyrrolidone | 0.1 to 20 | 0.5 to 15 | 1.0 to 10 | 2.5 | 1.6 |
| Optional additives | Up to 100 | Up to 100 | Up to 100 | Up to 100 | Up to 100 |

| | Formula 106 | Formula 107 | Formula 108 | Formula 109 | Formula 110 |
|---|---|---|---|---|---|
| Polar solvent a1) | 45 to 99 | 70 to 98 | 80 to 95 | 90 | 90 |
| Polymeric, anionic, amphiphilic thickener | 0.01 to 10 | 0.05 to 8.0 | 0.1 to 5.0 | 0.3 | 1.5 |
| Polyvinyl pyrrolidone | 0.1 to 20 | 0.5 to 15 | 1.0 to 10 | 2.5 | 1.6 |
| Nonanionic surfactant | 0.02 to 4.0 | 0.05 to 2.0 | 0.1 to 1.0 | 0.6 | 0.5 |
| Optional additives | Up to 100 | Up to 100 | Up to 100 | Up to 100 | Up to 100 |

| | Formula 111 | Formula 112 | Formula 113 | Formula 114 | Formula 115 |
|---|---|---|---|---|---|
| Polar solvent a1) | 45 to 99 | 70 to 98 | 80 to 95 | 90 | 90 |
| Polymeric, anionic, amphiphilic thickener | 0.01 to 10 | 0.05 to 8.0 | 0.1 to 5.0 | 0.3 | 1.5 |
| Vinyl pyrrolidone/vinyl acetate copolymer a3) | 0.1 to 20 | 0.5 to 15 | 1.0 to 10 | 2.5 | 1.6 |
| Optional additives | Up to 100 | Up to 100 | Up to 100 | Up to 100 | Up to 100 |

| | Formula 116 | Formula 117 | Formula 118 | Formula 119 | Formula 120 |
|---|---|---|---|---|---|
| Polar solvent a1) | 45 to 99 | 70 to 98 | 80 to 95 | 90 | 90 |
| Polymeric, anionic, amphiphilic thickener a2) | 0.01 to 10 | 0.05 to 8.0 | 0.1 to 5.0 | 0.3 | 1.5 |
| Vinyl pyrrolidone/vinyl acetate copolymer a3) | 0.1 to 20 | 0.5 to 15 | 1.0 to 10 | 2.5 | 1.6 |
| Nonanionic surfactant a4) | 0.02 to 4.0 | 0.05 to 2.0 | 0.1 to 1.0 | 0.6 | 0.5 |
| Optional additives | Up to 100 | Up to 100 | Up to 100 | Up to 100 | Up to 100 |

| | Formula 121 | Formula 122 | Formula 123 | Formula 124 | Formula 125 |
|---|---|---|---|---|---|
| Polar solvent a1) | 45 to 99 | 70 to 98 | 80 to 95 | 90 | 90 |
| Acrylates/steareth-20 methacrylate copolymer | 0.01 to 10 | 0.05 to 8.0 | 0.1 to 5.0 | 0.3 | 1.5 |
| Polyvinyl pyrrolidone | 0.1 to 20 | 0.5 to 15 | 1.0 to 10 | 2.5 | 1.6 |
| Optional additives | Up to 100 | Up to 100 | Up to 100 | Up to 100 | Up to 100 |

| | Formula 126 | Formula 127 | Formula 128 | Formula 129 | Formula 130 |
|---|---|---|---|---|---|
| Polar solvent a1) | 45 to 99 | 70 to 98 | 80 to 95 | 90 | 90 |
| Acrylates/steareth-20 methacrylate copolymer | 0.01 to 10 | 0.05 to 8.0 | 0.1 to 5.0 | 0.3 | 1.5 |
| Vinyl pyrrolidone/vinyl acetate copolymer a3) | 0.1 to 20 | 0.5 to 15 | 1.0 to 10 | 2.5 | 1.6 |
| Optional additives | Up to 100 | Up to 100 | Up to 100 | Up to 100 | Up to 100 |

| | Formula 131 | Formula 132 | Formula 133 | Formula 134 | Formula 135 |
|---|---|---|---|---|---|
| Polar solvent a1) | 45 to 99 | 70 to 98 | 80 to 95 | 90 | 90 |
| Acrylates/steareth-20 methacrylate | 0.01 to 10 | 0.05 to 8.0 | 0.1 to 5.0 | 0.3 | 1.5 |
| Polyvinyl pyrrolidone | 0.1 to 20 | 0.5 to 15 | 1.0 to 10 | 2.5 | 1.6 |
| Optional additives | Up to 100 | Up to 100 | Up to 100 | Up to 100 | Up to 100 |

| | Formula 136 | Formula 137 | Formula 138 | Formula 139 | Formula 140 |
|---|---|---|---|---|---|
| Polar solvent a1) | 45 to 99 | 70 to 98 | 80 to 95 | 90 | 90 |
| Acrylates/steareth-20 methacrylate | 0.01 to 10 | 0.05 to 8.0 | 0.1 to 5.0 | 0.3 | 1.5 |
| Vinyl pyrrolidone/vinyl acetate copolymer a3) | 0.1 to 20 | 0.5 to 15 | 1.0 to 10 | 2.5 | 1.6 |
| Optional additives | Up to 100 | Up to 100 | Up to 100 | Up to 100 | Up to 100 |

| | Formula 141 | Formula 142 | Formula 143 | Formula 144 | Formula 145 |
|---|---|---|---|---|---|
| Polar solvent a1) | 45 to 99 | 70 to 98 | 80 to 95 | 90 | 90 |
| Acrylates/steareth-20 itaconate copolymer | 0.01 to 10 | 0.05 to 8.0 | 0.1 to 5.0 | 0.3 | 1.5 |

|  | | | | | |
|---|---|---|---|---|---|
| Polyvinyl pyrrolidone | 0.1 to 20 | 0.5 to 15 | 1.0 to 10 | 2.5 | 1.6 |
| Optional additives | Up to 100 | Up to 100 | Up to 100 | Up to 100 | Up to 100 |

|  | Formula 146 | Formula 147 | Formula 148 | Formula 149 | Formula 150 |
|---|---|---|---|---|---|
| Polar solvent a1) | 45 to 99 | 70 to 98 | 80 to 95 | 90 | 90 |
| Acrylates/steareth-20 itaconate copolymer | 0.01 to 10 | 0.05 to 8.0 | 0.1 to 5.0 | 0.3 | 1.5 |
| Vinyl pyrrolidone/vinyl acetate copolymer a3) | 0.1 to 20 | 0.5 to 15 | 1.0 to 10 | 2.5 | 1.6 |
| Optional additives | Up to 100 | Up to 100 | Up to 100 | Up to 100 | Up to 100 |

|  | Formula 151 | Formula 152 | Formula 153 | Formula 154 | Formula 155 |
|---|---|---|---|---|---|
| Polar solvent a1) | 45 to 99 | 70 to 98 | 80 to 95 | 90 | 90 |
| Acrylates/$C_{10-30}$ alkyl acrylate crosspolymer | 0.01 to 10 | 0.05 to 8.0 | 0.1 to 5.0 | 0.3 | 1.5 |
| Polyvinyl pyrrolidone | 0.1 to 20 | 0.5 to 15 | 1.0 to 10 | 2.5 | 1.6 |
| Optional additives | Up to 100 | Up to 100 | Up to 100 | Up to 100 | Up to 100 |

|  | Formula 156 | Formula 157 | Formula 158 | Formula 159 | Formula 160 |
|---|---|---|---|---|---|
| Polar solvent a1) | 45 to 99 | 70 to 98 | 80 to 95 | 90 | 90 |
| Acrylates/$C_{10-30}$ alkyl acrylate crosspolymer | 0.01 to 10 | 0.05 to 8.0 | 0.1 to 5.0 | 0.3 | 1.5 |
| Vinyl pyrrolidone/vinyl acetate copolymer a3) | 0.1 to 20 | 0.5 to 15 | 1.0 to 10 | 2.5 | 1.6 |
| Optional additives | Up to 100 | Up to 100 | Up to 100 | Up to 100 | Up to 100 |

Very especially preferred cosmetic preparations include, in addition the previously described components a1) to a5), only slight quantities of other active ingredients and adjuvants. Cosmetic preparations, characterized in that the cosmetic preparation consists, with respect to their total weight, of at 80 wt %, preferably at least 90 wt %, and particularly at least 97 wt % of the components a1), a2), a3), and a4) and, if present, a5) are especially preferred due to their simple manufacturability and good cosmetic effect. Very especially preferred cosmetic preparations consist, with respect to their total weight, of at least 80 wt %, preferably at least 90 wt %, and particularly at least 97 wt % of the components a1), a2), and a3).

As stated at the outset, the cosmetic preparations a) according to the invention are especially suitable for application by means of a flash evaporation device. Another object of the present invention is therefore the use of a cosmetic preparation a) with a viscosity from 5,000 to 1,000,000 mPas including, with respect to its total weight,
a1) 60 to 98 wt % of at least one polar solvent;
a2) 0.01 to 10 wt % of at least one thickener;
as material for processing in a flash evaporation device.

Another object of the present invention is the use of a product according to the invention for the application of a cosmetic preparation a) to keratin-containing fibers, particularly human hairs, or for the temporary deformation of keratin-containing fibers, particularly human hairs.

A method for temporarily deforming keratin-containing fibers, particularly human hairs, in which a flash evaporation device is used to apply to the keratin-containing fibers a cosmetic preparation a) with a viscosity from 5,000 to 1,000,000 mPas including, with respect to its total weight,
a1) 60 to 98 wt % of at least one polar solvent;
a2) 0.01 to 10 wt % of at least one thickener;
is another object of the present invention. The cosmetic preparation a) is preferably converted by means of the flash evaporation device into an atomized spray that is then applied to the keratin-containing fibers.

In order to achieve a sufficient spray effect, the cosmetic preparation a) is preferably heated to temperatures above the boiling point of the polar solvent or solvent mixture included in the cosmetic preparation a).

If the polar solvent is water or solvent mixtures with a water content of greater than 50 wt % (with respect to the total weight of the solvent mixture), the cosmetic preparation is preferably heated to temperatures above 100° C., preferably to temperatures from 100° C. and 240° C., especially preferably to temperatures from 140° C. to 160° C.

In all cases in which the polar solvent is water or solvent mixtures with a water content of greater than 50 wt % (with respect to the total weight of the solvent mixture), the overpressure achieved through the heating of the cosmetic preparation a) is preferably between 1.1 and 8 bar, preferably between 1.2 and 4 bar.

A preferred object of the application is a method for changing the color of keratin-containing fibers, particularly human hairs, in which a flash evaporation device is used to apply to the keratin-containing fibers a cosmetic preparation a) containing, with respect to its total weight,
a1) 60 to 98 wt % polar solvent;
a2) 0.01 to 10 wt % of at least one thickener;
wherein
- a portion of the cosmetic preparation a) located in a reservoir is transferred from this reservoir, the interior pressure of which corresponds to the ambient pressure, to a container b1);
- the access between reservoir and container b1) is then interrupted by a component for flow regulation by means of which the flow of the cosmetic preparation a) from the reservoir into the container b1) can be interrupted;
- the cosmetic preparation a) located in the container b1), which is sealed off against the environment, is heated by means of a heating device, so that the pressure on the interior of the container b1) increases to values above the ambient pressure, preferably to values between 1.1 and 8 bar, particularly to values between 1.2 and 4 bar;

the container b1), which is under a pressure above ambient pressure, is then relieved in such a way that enables at least a portion, preferably at least 50 wt %, more preferably at least 80 wt %, and particularly at least 90 wt % of the cosmetic preparation located in the container b1) to be released from the container b1) into the environment under reduction of the pressure prevailing in the container b1) at the moment the container was opened.

The releasing of the cosmetic preparation a) into the environment preferably occurs under formation of an atomized spray of the cosmetic preparation a).

The cosmetic preparation a) released from the container b1) is preferably applied to keratinic fibers, particularly human hairs.

Methods over the course of which the cosmetic preparation released from the container b1) before application to the keratinic fibers is conducted through a nozzle are especially preferred.

As regards other preferred embodiments of the uses and method according to the invention, the remarks regarding the cosmetic preparations a) according to the invention and the flash evaporation device b) apply mutatis mutandis.

To summarize, the agents, uses, and method according to the invention and several of the preferred embodiments thereof are characterized by the following points:

A comprehensive product, comprising
a) a cosmetic preparation with a viscosity from 5,000 to 1,000,000 mPas which includes, with respect to its total weight,
   a1) 60 to 98 wt % of at least one polar solvent;
   a2) 0.01 to 10 wt % of at least one thickener;
b) a device for flash-evaporating the cosmetic preparation a).

A cosmetic product according to point 1, characterized in that the flash-evaporating device comprises a container b1) and a heating device b2) and is embodied such that
   the cosmetic preparation can be received in the interior space of the container b1),
   the interior of the container b1) filled at least in part with the cosmetic preparation a) can be sealed,
   the cosmetic preparation a) in the closed interior of the container b1) can be heated by means of the heating device b2), thereby increasing the pressure,
   the heated cosmetic preparation a) can be released from the interior of the container b1) under pressure reduction into the environment.

The cosmetic product according to any one of the preceding points, characterized in that the viscosity of the cosmetic preparation a) is 10,000 to 500,000 mPas, preferably 20,000 to 250,000 mPas.

The cosmetic product according to any one of the preceding points, characterized in that the proportion by weight of the polar solvent a1) to the total weight of the cosmetic preparation a) is 70 to 98 wt %, preferably 80 to 95 wt %.

The cosmetic product according to any one of the preceding points, characterized in that the polar solvent a1) has a boiling temperature (20° C., 1013 mbar) between 50 and 110° C., preferably between 70 and 105° C.

The cosmetic product according to any one of the preceding points, characterized in that the polar solvent a1) is selected from the group of ethanol, isopropanol, and water.

The cosmetic product according to any one of the preceding points, characterized in that the proportion by weight of water and ethanol to the total weight of the polar solvent a1) is preferably at least 60 wt %, more preferably at least 80 wt %, especially preferably at least 90 wt %, and particularly at least 95 wt %.

The cosmetic product according to any one of the preceding points, characterized in that the proportion by weight of water to the total weight of the polar solvent a1) is preferably greater than 80 wt %, preferably greater than 88 wt %, and particularly greater than 92 wt %.

The cosmetic product according to any one of the preceding points, characterized in that the proportion by weight of the ethanol to the total weight of the cosmetic preparation is preferably at least 55 wt %, more preferably 10 to 55 wt %, especially preferably 25 to 55 wt %, and particularly 40 to 55 wt %.

The cosmetic product according to any one of the preceding points, characterized in that the polar solvent a1) comprises water and ethanol and the weight ratio of water to ethanol is 5:1 to 1:5, preferably 2:1 to 1:2, and particularly 5:4 to 4:5.

The cosmetic product according to any one of the preceding points, characterized in that the proportion by weight of the thickener a2) to the total weight of the cosmetic preparation a) is 0.05 to 8.0 wt %, preferably 0.1 to 5.0 wt %.

The cosmetic product according to any one of the preceding points, characterized in that the thickener a2) is selected from the group of the polymeric organic thickeners.

The cosmetic product according to any one of the preceding points, characterized in that the thickener a2) is selected from the group of the polymeric, anionic, amphiphilic thickeners.

The cosmetic product according to any one of the preceding points, characterized in that the thickener a2) is selected from the group of the compounds with INCI designation carbomer, acrylates/steareth-20 methacrylate copolymer, acrylates/steareth-20 methacrylate crosspolymer, acrylates/steareth-20 itaconate copolymer, and acrylates/$C_{10-30}$ alkyl acrylate crosspolymer.

The cosmetic product according to any one of the preceding points, characterized in that the thickener a2) is selected from the group of the acrylic acid homopolymers.

The cosmetic product according to any one of the preceding points, characterized in that the cosmetic preparation a) includes, with respect to its total weight, 0.1 to 20 wt %, preferably 0.5 to 15 wt %, and particularly from 1.0 to 10 wt % of a film-forming polymer a3).

The cosmetic product according to point 16, characterized in that the film-forming polymer a3) is selected from the group of the nonionic polymers, preferably from the group of the polyvinyl pyrrolidone and vinyl pyrrolidone/vinyl acetate copolymers, more preferably of the vinyl pyrrolidone/vinyl acetate copolymers.

The cosmetic product according to point 16, characterized in that the film-forming polymer a3) is selected from the group of the anionic polymers, preferably from the group of the copolymers of acrylic acid and methacrylic acid.

The cosmetic product according to point 14, characterized in that the film-forming polymer a3) is selected from the group of the copolymers of methacryloylethyl-N,N-dimethylamine oxide.

The cosmetic product according to point 14, characterized in that the film-forming polymer a3) is selected from the group of the copolymers of i) N-tert-octylacrylamide, ii) acrylic acid, iii) tert.-butylaminoethyl methacrylate, iv) as well as, optionally, other monomers.

The cosmetic product according to any one of the preceding points, characterized in that the cosmetic preparation a) includes, with respect to its total weight, 0.02 to 4.0 wt %, preferably 0.05 to 2.0 wt %, and particularly 0, 1 to 1.0 wt % of a nonionic surfactant a4).

The cosmetic product according to point 20, characterized in that the nonionic surfactant a4) is selected from the group of the PEG derivatives of hydrated castor oil, especially preferably from the group of PEG-40 hydrogenated castor oil and PEG-60 hydrogenated castor oil.

The cosmetic product according to any one of the preceding points, characterized in that the cosmetic preparation a) includes, with respect to its total weight, 0.05 to 3.0 wt %, preferably 0.1 to 2.0 wt %, and particularly 0.2 to 1.0 wt % of a cationic surfactant a5).

The cosmetic product according to point 22, characterized in that the cationic surfactant a5) is selected from the groups of the quaternary ammonium compounds, the esterquats, and the amidoamines, preferably from the group of the quaternary ammonium compounds, particularly from the group of the ($C_{12}$ to $C_{18}$) alkyltrimethylammonium salts.

The cosmetic product according to any one of the preceding points, characterized in that the cosmetic preparation a) includes, with respect to its total weight, at least to 80 wt %, preferably to 90 wt %, and particularly at least 97 wt % of the components a1), a2), and a3).

The cosmetic product according to any one of the preceding points, characterized in that the cosmetic preparation a) includes, with respect to its total weight, at least 80 wt %, preferably 90 wt %, and particularly at least 97 wt % of the components a1), a2), a3), a4) and, if present, a5).

A use of a cosmetic preparation a) with a viscosity from 5,000 to 1,000,000 mPas which includes, with respect to its total weight,
a1) 60 to 98 wt % of at least one polar solvent;
a2) 0.01 to 10 wt % of at least one thickener;
as material for processing in a flash evaporation device.

The use of a product according to any one of points 1 to 25 for application of a cosmetic preparation a) to keratin-containing fibers, particularly human hairs.

The use of a product according to any one of points 1 to 25 for temporarily shaping keratin-containing fibers, particularly human hairs.

A method for temporarily deforming keratin-containing fibers, particularly human hairs, in which a flash evaporation device is used to apply to the keratin-containing fibers a cosmetic preparation a) with a viscosity from 5,000 to 1,000,000 mPas including, with respect to its total weight,
a1) 60 to 98 wt % of at least one polar solvent;
a2) 0.01 to 10 wt % of at least one thickener.

The method according to point 29, characterized in that
a portion of the cosmetic preparation a) located in a reservoir is transferred from this reservoir, the interior pressure of which corresponds to the ambient pressure, to a container b1);
the access between reservoir and container b1) is then interrupted by a component for flow regulation by means of which the flow of the cosmetic preparation a) from the reservoir into the container b1) can be interrupted;
the cosmetic preparation a) located in the container b1), which is sealed off against the environment, is heated by means of a heating device, so that the pressure on the interior of the container b1) increases to values above the ambient pressure, preferably to values between 1.1 and 8 bar, particularly to values between 1.2 and 4 bar;
the container b1), which is under a pressure above ambient pressure, is then relieved in such a way that enables at least a portion, preferably at least 50 wt %, more preferably at least 80 wt %, and particularly at least 90 wt % of the cosmetic preparation located in the container b1) to be released from the container b1) into the environment under reduction of the pressure prevailing in the container b1) at the moment the container was opened.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A comprehensive product, comprising:
a) a cosmetic preparation with a viscosity from 5,000 to 1,000,000 mPas which includes, with respect to its total weight,
a1) 60 to 98 wt % of at least one polar solvent;
a2) 0.01 to 10 wt % of at least one thickener;
b) a device for flash-evaporating the cosmetic preparation a), wherein the flash-evaporating device comprises a container b1) a valve, and a heating device b2) and is configured such that
the cosmetic preparation can be received in the interior space of the container b1),
the interior of the container b1) filled at least in part with the cosmetic preparation a) can be sealed,
the cosmetic preparation a) in the closed interior of the container b1) is heated by means of the heating device b2) to a temperature of 140° C. and 160° C., thereby increasing the pressure,
the heated cosmetic preparation a) can be released from the interior of the container b1) under pressure reduction into the environment.

2. The cosmetic product as set forth in claim 1, wherein the viscosity of the cosmetic preparation a) is 10,000 to 250,000 mPas.

3. The cosmetic product as set forth in claim 1, wherein the viscosity of the cosmetic preparation a) is 20,000 to 250,000 mPas.

4. The cosmetic product as set forth in claim 1, wherein the proportion by weight of the polar solvent a1) to the total weight of the cosmetic preparation a) is 70 to 98 wt %.

5. The cosmetic product as set forth in claim 1, wherein the proportion by weight of the polar solvent a1) to the total weight of the cosmetic preparation a) is 80 to 95 wt %.

6. The cosmetic product as set forth in claim 1, wherein the proportion by weight of the thickener a2) to the total weight of the cosmetic preparation a) is 0.05 to 8.0 wt %.

7. The cosmetic product as set forth in claim 1, wherein the proportion by weight of the thickener a2) to the total weight of the cosmetic preparation a) is 0.1 to 5.0 wt %.

8. The cosmetic product as set forth in claim 1, wherein the thickener a2) is a polymeric organic thickeners.

9. The cosmetic product as set forth in claim 1, wherein the cosmetic preparation a) includes, with respect to its total weight, 0.1 to 20 wt % of a film-forming polymer a3).

10. The cosmetic product as set forth in claim 1, wherein the cosmetic preparation a) includes, with respect to its total weight, 0.5 to 15 wt % of a film-forming polymer a3).

11. The cosmetic product as set forth in claim 1, wherein the cosmetic preparation a) includes, with respect to its total weight, 1.0 to 10 wt % of a film-forming polymer a3).

12. A method for temporarily deforming keratin-containing fibers, comprising:
  applying to keratin-containing fibers the cosmetic preparation of claim 1 using a flash evaporation device.

* * * * *